(12) United States Patent
Tao et al.

(10) Patent No.: US 11,406,840 B2
(45) Date of Patent: Aug. 9, 2022

(54) SYSTEMS AND METHODS FOR REDUCING THE VISCOSITY OF BLOOD, SUPPRESSING TURBULENCE IN BLOOD CIRCULATION, AND CURING ROULEAUX

(71) Applicant: Temple University of the Commonwealth System of Higher Education, Philadelphia, PA (US)

(72) Inventors: Rongjia Tao, Cherry Hill, NJ (US); Hong Tang, Philadelphia, PA (US); Xiaojun Xu, Philadelphia, PA (US); Kazi M. Tawhid-Al-Islam, Philadelphia, PA (US); Enpeng Du, Kennett Square, PA (US)

(73) Assignee: Temple University of the Commonwealth System of Higher Education, Philadelphia, PA (US)

( * ) Notice: Subject to any disclaimer, the term of this patent is extended or adjusted under 35 U.S.C. 154(b) by 527 days.

(21) Appl. No.: 16/330,578

(22) PCT Filed: Nov. 1, 2017

(86) PCT No.: PCT/US2017/059446
§ 371 (c)(1),
(2) Date: Mar. 5, 2019

(87) PCT Pub. No.: WO2018/085330
PCT Pub. Date: May 11, 2018

(65) Prior Publication Data
US 2021/0283410 A1    Sep. 16, 2021

Related U.S. Application Data

(60) Provisional application No. 62/416,270, filed on Nov. 2, 2016.

(51) Int. Cl.
*A61N 2/00* (2006.01)
*A61N 2/06* (2006.01)

(52) U.S. Cl.
CPC ............... *A61N 2/004* (2013.01); *A61N 2/06* (2013.01)

(58) Field of Classification Search
CPC ....... A61N 2/02; A61N 2/06; A61F 2005/418; A61F 5/41
See application file for complete search history.

(56) References Cited

U.S. PATENT DOCUMENTS

| 5,788,624 A | 8/1998 | Lu et al. |
| 9,050,277 B2 | 6/2015 | Li et al. |

(Continued)

FOREIGN PATENT DOCUMENTS

| CN | 1666790 A | 9/2005 |
| CN | 102350021 A | 2/2012 |

(Continued)

OTHER PUBLICATIONS

R Tao and K Huang. "Reducing Blood Viscosity with Magnetic Fields." Physical Review E 84, 011905 (2011). (Year: 2011).*

(Continued)

*Primary Examiner* — Christine H Matthews
*Assistant Examiner* — Joshua Daryl D Lannu
(74) *Attorney, Agent, or Firm* — RatnerPrestia (57) ABSTRACT

Systems and methods for reducing blood viscosity along a flow direction, suppressing turbulence in blood flow, and treating rouleaux are disclosed. One method includes applying a unidirectional magnetic field to a flow of blood in a direction parallel or antiparallel to a direction of the flow of blood, and maintaining the application of the unidirectional magnetic field to the flow of blood until a blood viscosity along the direction of the flow of blood is reduced and/or the (Continued)

High Viscosity    Aggregate the Cells    Low viscosity in flow direction
High viscosity perpendicular to the flow turbulence in the blood flow is suppressed. One system includes an annular magnet sized to encircle a portion of a patient's body. The magnet is adapted to generate a unidirectional magnetic field in a region within the annular magnet. The unidirectional magnetic field has a strength sufficient to reduce the blood viscosity in the portion of the patient's body and/or suppress turbulence in the blood flow by a predetermined amount. The system will also break rouleaux for patients with rouleaux, but the process will take more time. The blood viscosity reduction and turbulence suppression can make the blood flow laminar, lower the patient's blood pressure, cure hypertension, diminish heart murmur, and prevent development of astherosclerosis plaque in blood vessels. The curing rouleaux will improve the patient's blood oxygen function.

21 Claims, 13 Drawing Sheets

(56) References Cited

U.S. PATENT DOCUMENTS

| | | | |
|---|---|---|---|
| 2002/0198435 | A1 | 12/2002 | Paturu |
| 2003/0171640 | A1 | 9/2003 | Canedo |
| 2005/0107656 | A1 | 5/2005 | Jang et al. |
| 2010/0280303 | A1* | 11/2010 | Dietz ............... A61N 2/00 600/12 |

FOREIGN PATENT DOCUMENTS

| | | |
|---|---|---|
| JP | 09502623 A | 3/1997 |
| JP | 2012529485 A | 11/2012 |

OTHER PUBLICATIONS

Chinese Office Action for Chinese Application No. 201780031721.0, dated Apr. 26, 2021, 7 pages.
Tao et al., "Reducing blood viscosity with magnetic fields" Physical Review, vol. E84, 011905, 6 pages (2011).
International Search Report and Written Opinion for International Application No. PCT/US2017/059446, dated Nov. 1, 2017, 6 pages.
International Preliminary Report on Patentability for International Application No. PCT/US2017/059446, dated May 7, 2019, 6 pages.
Japanese Notice of Reasons for Rejection for Japanese Application No. 2018-560849, dated Sep. 28, 2021 with translation, 10 pages.

* cited by examiner

SYSTEMS AND METHODS FOR REDUCING THE VISCOSITY OF BLOOD, SUPPRESSING TURBULENCE IN BLOOD CIRCULATION, AND CURING ROULEAUX

CROSS-REFERENCE TO RELATED APPLICATIONS

This application is a U.S. National Phase Application of PCT International Application PCT/US2017/059446, filed Nov. 1, 2017, and claims the benefit of priority of, U.S. Provisional Application No. 62/416,270, entitled SYSTEMS AND METHODS FOR REDUCING THE VISCOSITY OF BLOOD, suppressing turbulence in blood circulation, and CURING rouleaux, filed on 2 Nov. 2016, the contents of which are incorporated herein by reference in their entirety for all purposes.

FIELD OF THE INVENTION

The present invention relates generally to medical treatment, and particularly, to systems and methods incorporating magnetic fields to reduce blood viscosity, suppress turbulence in blood circulation, and treat cardiovascular diseases such as rouleaux.

BACKGROUND OF THE INVENTION

Heart attacks and strokes are the leading causes of death in many industrial countries. Recent research indicates that there is one common thread, high blood viscosity, which links all cardiovascular diseases. Moreover, turbulence in blood flow or disturbed blood flow makes different regions of the vasculature vulnerable to development of atherosclerotic plaque, and, in return, growing plaque further makes disturbed blood flow worse. Turbulence can also be responsible for systolic ejection murmurs. Since turbulence in blood circulation requires much heavier workload from heart, it could trigger heart attacks and other cardiovascular ailments.

Figure 1A:
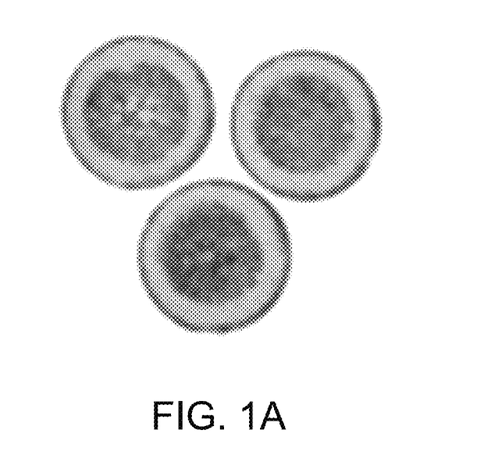
FIGS. 1A and 1B depict images of red blood cells (a) in a normal separated state or (b) in a rouleau, respectively.
Figure 1B:
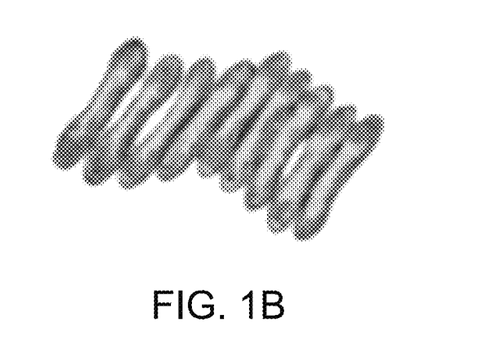

One unique blood disease is known as Rouleaux. Rouleaux is a term referring to stacks of red blood cells along their flat surfaces (or in other words, axial stacks of red blood cells). FIG. 1A depicts red blood cells in a normal separated state; FIG. 1B depicts a rouleau of red blood cells. When the flat surfaces of red blood cells stick to each other to form a rouleau, the cells are obstructed from performing their principal function properly in delivering oxygen to the body tissues via the blood flow in circulation. Rouleaux is a serious disease, causing generalized weakness and pains in the whole body, swelling of orbits, deterioration of vision, and symptoms of acute confusion.

Currently, the only method to reduce the blood viscosity is to take medicine, such as aspirin, which inhibit the tendency of blood to clot. However, aspirin has side effects: in high doses, it can lead to stomach bleeding, ulcers, and even tinnitus. In addition, using medicine to reduce the blood viscosity does not help to suppress turbulence in blood flow. In fact, the turbulence may worsen because the Reynolds number is increased as a result of the reduced blood viscosity by medicine. In the case of rouleaux, due to the number of different potential causes, effective rouleaux treatment can be difficult.

In view of the above, improved systems and methods of reducing blood viscosity, suppressing turbulence in blood flow, and treating rouleaux are desired.

SUMMARY OF THE INVENTION

Aspects of the present invention are related to systems and methods for reducing blood viscosity along the flow direction, suppressing turbulence in blood flow, and treating rouleaux. As the result of blood viscosity reduction and turbulence suppression, the blood flow becomes laminar, the patient's blood pressure is lowered, heart murmur is diminished, and development of astherosclerosis plaque in blood vessels is prevented. The curing rouleaux also improves the patient's blood oxygen function.

In accordance with one aspect of the present invention, a method for reducing blood viscosity and/or suppressing turbulence in blood flow is disclosed. The method includes applying a unidirectional magnetic field to a flow of blood in a direction parallel or antiparallel to a direction of the flow of blood, and maintaining the application of the unidirectional magnetic field to the flow of blood until a blood viscosity along the direction of the flow of blood is reduced by a predetermined amount and/or the turbulence in the blood flow is suppressed.

In accordance with another aspect of the present invention, a system for reducing blood viscosity and/or suppressing turbulence in blood flow is disclosed. The system includes an annular magnet sized to encircle a portion of a patient's body. The magnet is adapted to generate a unidirectional magnetic field in a region within the annular magnet. The unidirectional magnetic field has a strength sufficient to reduce the blood viscosity in the portion of the patient's body by a predetermined amount and/or suppress turbulence in the blood flow by a predetermined amount.

In accordance with yet another aspect of the present invention, a method for treating rouleaux is disclosed. The method includes applying a unidirectional magnetic field to blood containing the rouleaux, and maintaining the application of the unidirectional magnetic field to the blood until the rouleaux are separated.

When a strong magnetic field is applied parallel or antiparallel to the blood flow, red blood cells are polarized and aggregated into short chains along the flow direction. Thus the effective blood viscosity becomes anisotropic; along the flow direction, the viscosity is significantly reduced. In the perpendicular to the flow, the viscosity is considerably increased, leading to turbulence suppression. With the both effect, the blood flow becomes laminar and greatly improved, the workload for the heart is reduced, and the heart attacks are prevented. In addition, the strong magnetic field breaks rouleaux, a serious vascular disease, makes the surface of red blood cells fully exposed, improves their oxygen function.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features may be arbitrarily expanded or reduced for clarity. Included in the drawings are the following figures.

DETAILED DESCRIPTION OF EXEMPLARY EMBODIMENTS OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

In accordance with aspects of the present invention, a strong magnetic field is applied to blood, preferably parallel or antiparallel to the blood flow direction, i.e. along the blood flow direction. Red blood cells contain hemoglobin, a red protein responsible for transporting oxygen. Hemoglobin contains iron, as a result of which the red blood cells carrying hemoglobin are paramagnetic, i.e., capable of being temporarily magnetically polarized under application of an external magnetic field. Therefore, under application of a strong magnetic field to blood, red blood cells are polarized.

It has been determined that, due to disc-shaped structure of red blood cells, the strongest polarization is along the diameter direction of each cell. As a result, in a strong magnetic field, the red cells will tilt to make their disk surface parallel to the magnetic field. Each red blood cell thereby obtains an induced dipole moment.

Red blood cells thus polarized in the magnetic field and aggregated into short chains in the diametric direction of the red cells. If the red cells are originally in rouleaux, the induced magnetic dipolar interaction force the red cells to break their surface connection first, then form short chains in the diametric direction of the red cells. In such chains, the surface of the cells would be fully exposed, allowing the red blood cells to perform their normal oxygen function. These short chains are aligned along the direction of blood flow. In this way, the blood viscosity becomes anisotropic: along the flow direction the viscosity is significantly reduced, but in the directions perpendicular to the flow, the viscosity is considerably increased. In this way, turbulence in blood flow is suppressed, since without motion in directions perpendicular to the flow, turbulence or disturbed flow cannot exist, and the turbulent blood flow becomes laminar. In addition, as the viscosity along the flow direction is reduced, the laminar blood flow is further improved. Keeping the blood flow laminar prevents development of astherosclerosis plaque in blood vessels.

By reducing blood viscosity along the flow direction and suppressing turbulence, aspects of the present invention greatly improve blood circulation, and reduce workload on the heart. The patient's blood pressure is lowered and heart murmur is diminished if the patient has heart murmur originally. While these effects are not permanent, they last for many hours and can be repeated. Therefore, repeated treatments with a suitable magnetic field as described herein can keep the blood viscosity within the normal range, maintain the laminar blood flow, and prevent heart attacks.

The exemplary embodiments described herein are particular suitable to the treatment of rouleaux. In particular, aspects of the present invention may operate to induce a magnetic repulsion between the stacked red blood cells of a rouleau. The strength of such a repulsive force depends on the strength of the external applied magnetic field. Under application of a sufficiently strong magnetic field, the force can exceed the weight of the red blood cells, and thereby be strong enough to break the stacking of the red blood cells in the rouleau. As the result of breaking up of the rouleau, the patient's blood oxygen function is improved.

While specific rouleaux treatments are described herein, it will be understood that the systems and methods described herein may be usable to treat other blood diseases or medical conditions in which the reduction of blood viscosity, suppressing turbulence in blood circulation, and/or the polarization of cells in the patient's blood achieves a medically beneficial result. Accordingly, it will be understood from the description herein that the following exemplary embodiments are not limited to being used to treat rouleaux.

Figure 2:
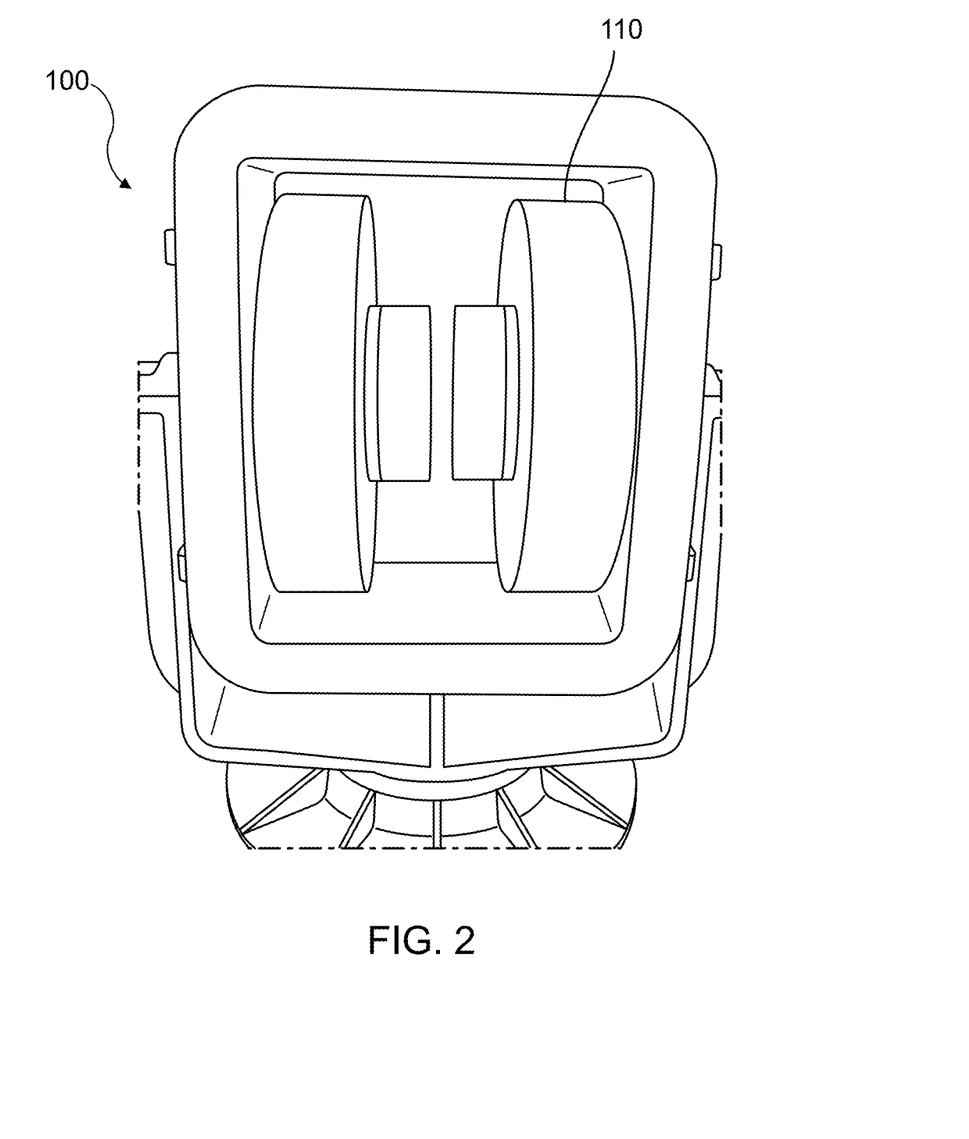
FIG. 2 depicts an exemplary system for reducing the viscosity of blood flow, suppressing turbulence, and curing rouleaux in accordance with aspects of the present invention.

Referring now to the drawings, FIG. 2 illustrates a system 100 for reducing the blood viscosity and/or suppressing turbulence in blood flow in accordance with aspects of the present invention. System 100 may be usable to treat rouleaux. As a general overview, system 100 includes a magnet 110. Additional details of system 100 are described below.

Magnet 110 generates a unidirectional magnetic field. As used herein, the term "unidirectional" refers to a magnetic field in which the direction of magnetic field lines is not changing (such as a degaussing magnetic field). Magnet 110 may be an electromagnet, as shown in FIG. 2, or may be a permanent magnet or superconducting magnet. Where magnet 110 is a permanent magnet, magnet 110 may be small enough to allow system 100 to include a harness or other structure to hold magnet 110 in position relative to the user. Where magnet 110 is an electromagnet or superconducting magnet, magnet 110 may be too big to be secured to or worn by the patient. In this embodiment, it may be necessary to provide an apparatus (such as a chair, bed, platform, etc.) to hold the patient in a fixed position relative to magnet 110.

In an exemplary embodiment, magnet 110 is an annular (or ring-shaped) magnet. In this embodiment, magnet 110 is adapted to generate the unidirectional field in a region within the magnet, i.e., axially through a center of the ring-shaped magnet.

Figure 3A:
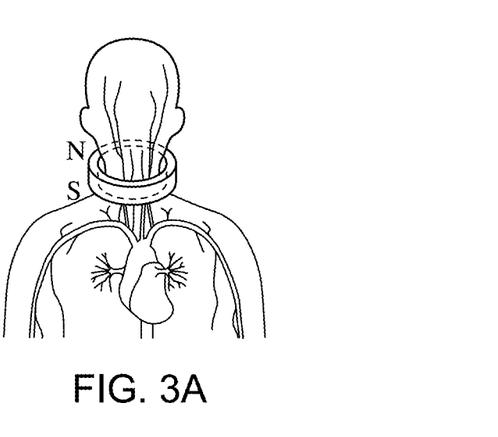
FIGS. 3A-3C depict exemplary blood flow treatments in accordance with aspects of the present invention.
Figure 3B:
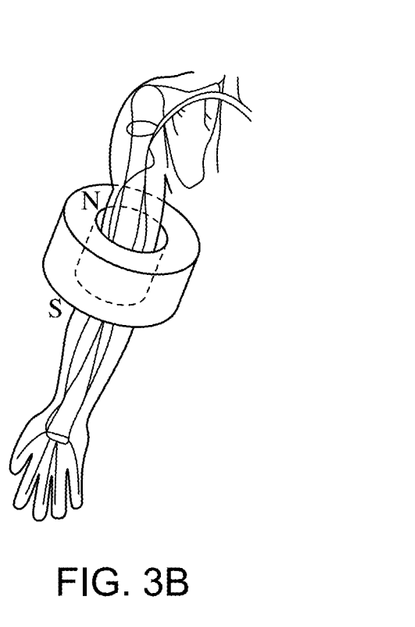
Figure 3C:
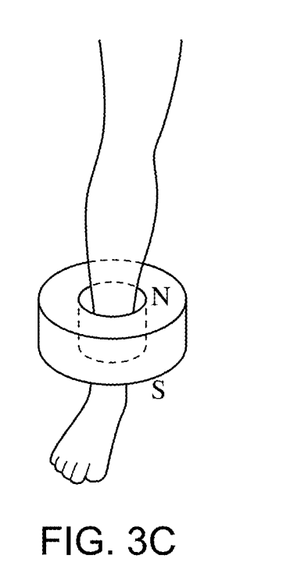

Magnet 110 has a size sufficient to encircle a portion of the patient's body. In this way, the unidirectional magnetic field generated by magnet 110 may be applied to a flow of blood within the patient. For example, magnet 110 may be sized to encircle the patient's neck, as shown in FIG. 3A; the patient's arm, as shown in FIG. 3B; and/or the patient's leg, as shown in FIG. 3C.

In an alternative embodiment, magnet 110 may be a bar magnet, or any other shape of magnet capable of applying a unidirectional magnetic field to a patient's blood flow. Magnet 110 has strength sufficient to reduce the blood viscosity in the patient's body by a predetermined amount, and/or to suppress turbulence in the patient's blood flow by a predetermined amount. Magnet 110 may have a strength sufficient to reduce blood viscosity to be within a normal range, such as about 3.0-4.0 cp. In an exemplary embodiment, magnet 110 generates a unidirectional magnetic field having a strength of 1 Tesla or greater. In one example, magnet 110 generates a 1.33 Tesla unidirectional magnetic field. A magnetic field having such a field strength or stronger field strength may be suitable to separate rouleaux within the patient's body.

Figure 4:
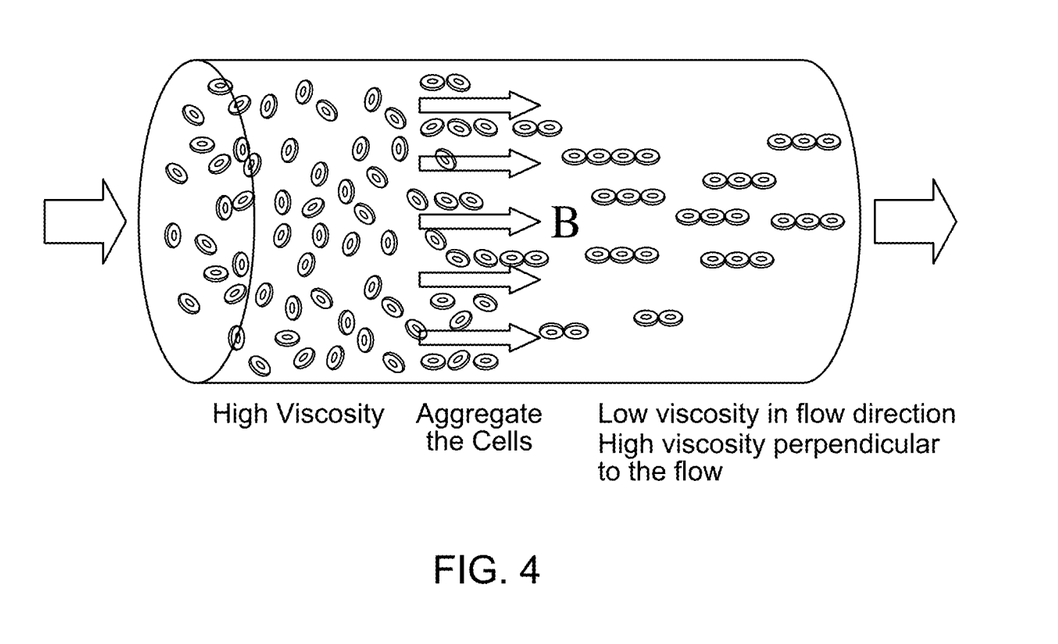
FIG. 4 depicts effects of blood flow treatment using the exemplary system of FIG. 2.

An exemplary operation of system 100 will now be described with reference to FIG. 4. FIG. 4 illustrates an exemplary flow of blood within a patient's body (such as within a patient's limb). Prior to treatment, red blood cells within a patient's blood flow are disorganized, as shown on the left side of FIG. 4. Due to the disorganization of red cells and their potential to collide with each other, the whole blood flow has a relatively higher effective viscosity. In addition, such blood may develop turbulent currents or eddies which deviate from the direction of blood flow. During treatment with system 100, magnet 110 applies a unidirectional magnetic field to the blood flow. As shown by arrows in FIG. 4, this magnetic field is applied parallel to the direction of blood flow. As a result of this field, red blood cells are polarized, and are aggregated into short chains in the diametric direction of the blood cells, as shown in the right side of FIG. 4. These short chains are aligned along the direction of flow of the blood. As a result, the blood viscosity is significantly reduced along the direction of blood flow, as the chains of red blood cells are streamlined along the flow direction.

On the other hand, the blood viscosity in the directions perpendicular to the flow is significantly increased as these short chains strongly resist any motion in the directions perpendicular to the flow. The blood flow becomes a laminar flow if it was turbulent before the application of magnetic field. After the application of magnetic field in FIG. 4, with sufficient time for the blood circulation, all blood within the patient's whole body will have reduced viscosity along the flow direction and any turbulence in blood circulation at any part of the body will be suppressed.

Figure 5:
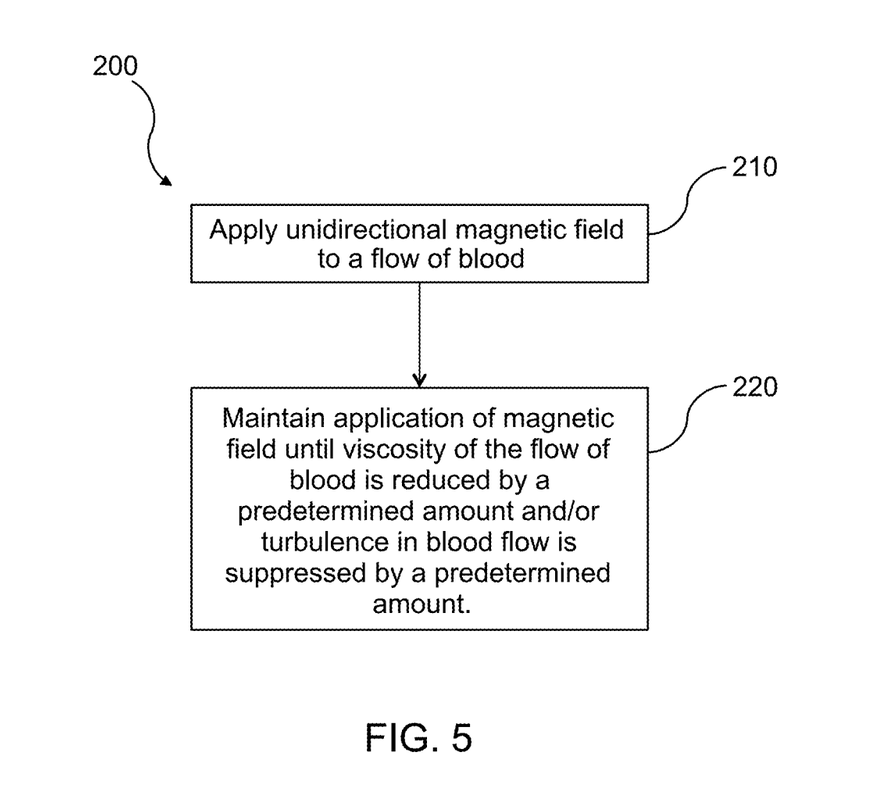
FIG. 5 depicts an exemplary method for reducing blood viscosity and suppressing turbulence in blood flow in accordance with aspects of the present invention.

FIG. 5 illustrates a method 200 for reducing the blood viscosity and/or suppressing turbulence in blood flow in accordance with aspects of the present invention. As a general overview, method 200 includes applying a magnetic field, and maintaining application of the magnetic field. Additional details of method 200 are described below with reference to system 100.

In step 210, a unidirectional magnetic field is applied to a flow of blood. The blood flow may be within the patient's body, or may be an extracorporeal flow of blood, such as may be found in hemodialysis. In an exemplary embodiment, magnet 110 encircles a patient's limb and applies a unidirectional magnetic field to a flow of blood within the patient's limb. The unidirectional magnetic field is applied in a direction parallel or antiparallel to a direction of the blood flow.

Figure 6A:
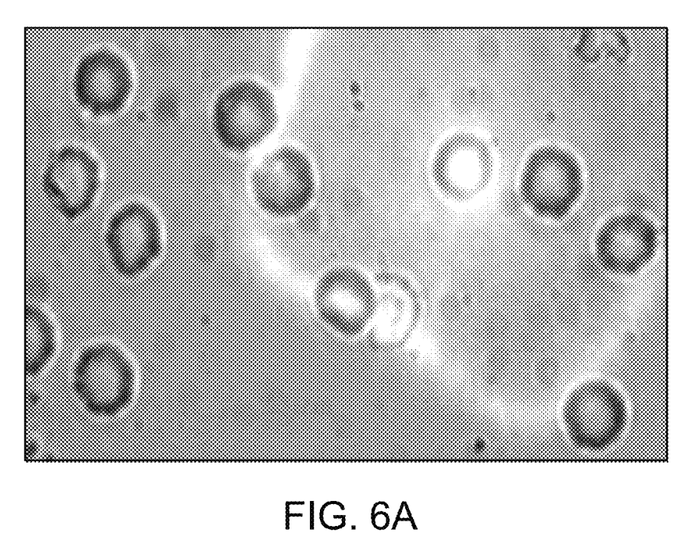
FIGS. 6A and 6B depict red blood cells (a) before and (b) after the blood flow treatment depicted in FIG. 5.
Figure 6B:
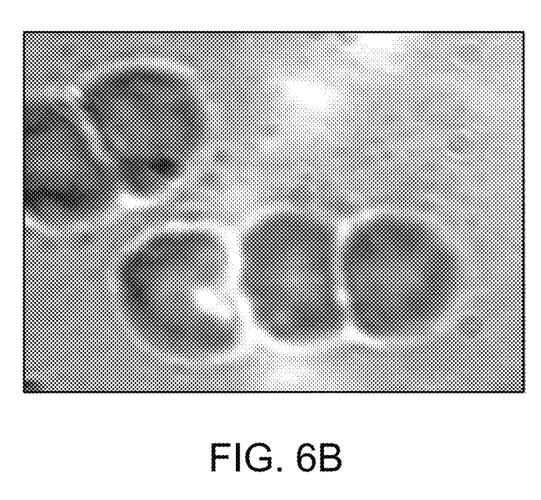

In step 220, the application of the unidirectional magnetic field to the blood flow is maintained until the effective blood viscosity is reduced by a predetermined amount. FIGS. 6A and 6B depict red blood cells before and after the performance of step 220, respectively. FIG. 6A shows that blood cells are separate and disorganized before treatment. As shown in FIG. 6B, the application of the unidirectional magnetic field has caused chains of blood cells to be formed along the direction of the unidirectional magnetic field, thereby resulting in the predetermined viscosity reduction. The duration of step 220 necessary to achieve the predetermined viscosity reduction is dependent on the predetermined amount of reduction desired, the strength of the unidirectional magnetic field, and the length of time the blood flow is exposed to the magnetic field. In one example, blood viscosity is kept within a normal range, for example, 3.0-4.0 cp. Therefore, an amount of viscosity reduction may depend on the original viscosity before the magnetic treatment. In some cases, a reduction in viscosity of 50% may be predetermined in order to reach the goal.

In an exemplary embodiment, the unidirectional magnetic field has a strength of 1 Tesla or greater, and more particularly, a strength of 1.33 Tesla. The unidirectional magnetic field may be applied to the blood sample for a predetermined period of time, e.g., four seconds. Longer periods of time, such as 20 seconds, 30 seconds, one minute, five minutes or more, may also be used. In case that the applied magnetic field is weaker, the application time may be longer. If the applied magnetic field is stronger, the required time may be shorter. In order to reduce the viscosity along the flow direction for all blood inside the patient's whole body and suppress turbulence in any part of blood circulation within the patient's body, with the arrangements in FIGS. 3A-3C, the application of magnetic field may be at least fifteen minutes or longer.

Figure 6C:
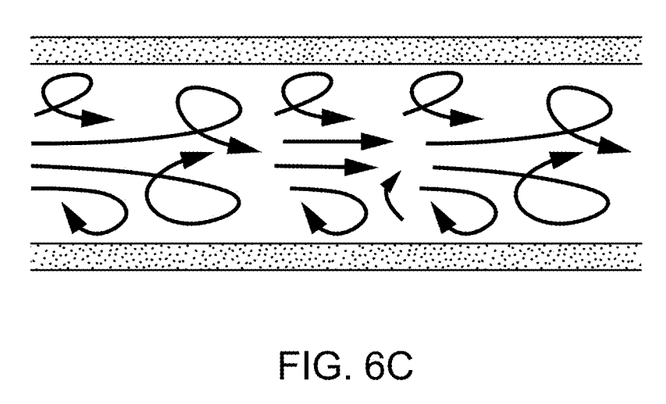
FIGS. 6C and 6D depict a flow of red blood cells (a) before suppression of turbulence and (b) after suppression of turbulence to create laminar blood flow.
Figure 6D:
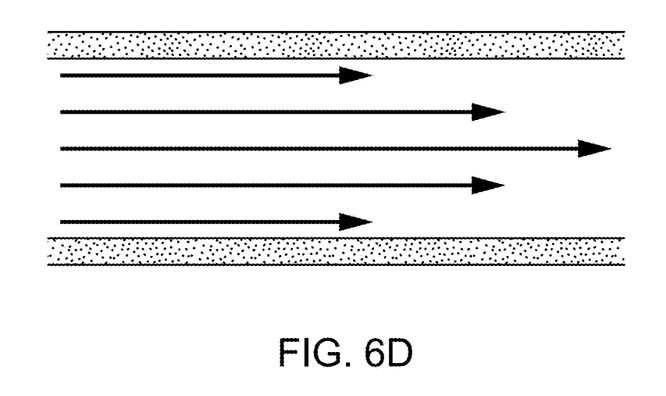

FIGS. 6C and 6D depict the blood flow before and after the performance of step 220, respectively. FIG. 6C shows that prior to application of the unidirectional magnetic field, the blood flow was originally turbulent. As shown in FIG. 6D, the application of the unidirectional magnetic field suppresses the turbulence and makes the blood flow laminar. The duration of step 220 necessary to achieve the turbulence suppression may be the same or different as the length of time required for viscosity reduction.

Figure 7:
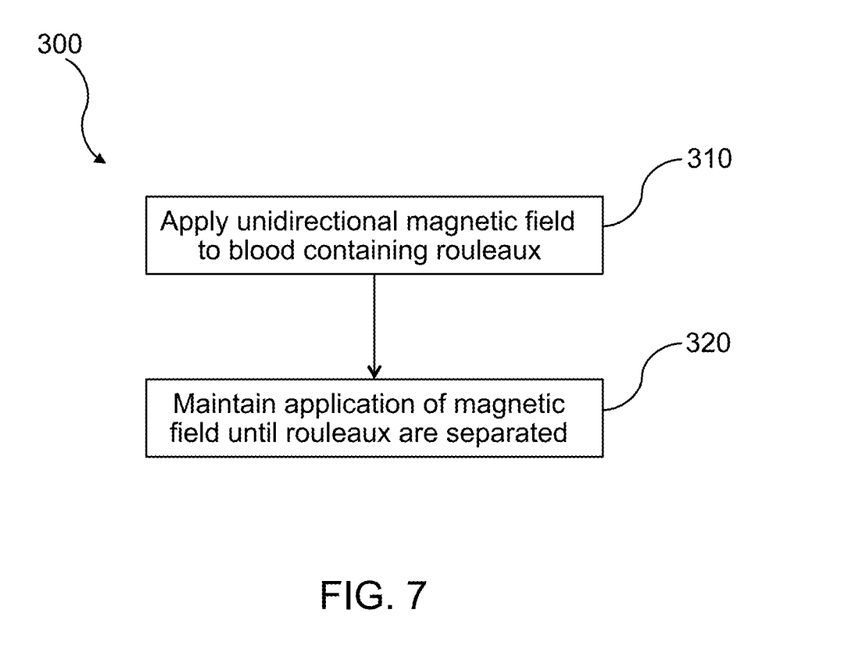
FIG. 7 depicts an exemplary method for treating rouleaux in accordance with aspects of the present invention.

FIG. 7 illustrates a method 300 for treating rouleaux in accordance with aspects of the present invention. As a general overview, method 300 includes applying a magnetic field, and maintaining application of the magnetic field. Additional details of method 300 are described below.

In step 310, a unidirectional magnetic field is applied to blood containing rouleaux. The blood may be part of a blood flow within the patient's body, may be an extracorporeal flow of blood, such as may be found in hemodialysis, or may be in a static (unflowing) reservoir of blood, such as may be used for blood transfusions. In an exemplary embodiment, magnet 110 encircles a patient's limb and applies a unidirectional magnetic field to a flow of blood within the patient's limb.

The unidirectional magnetic field may be applied in a direction parallel or antiparallel to a direction of the blood flow. Orienting the magnetic field lines to be parallel or antiparallel to the direction of blood flow may be desirable in order to avoid interference with blood flow by the aggregated chains of red blood cells.

Figure 8A:
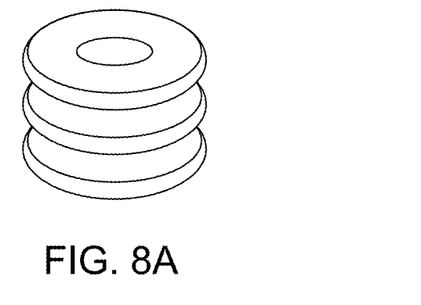
FIGS. 8A, 8B, 8C, and 8D depict a process for breaking up and curing rouleaux using the method of FIG. 7.
Figure 8B:
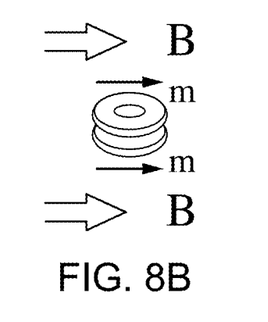
Figure 8C:
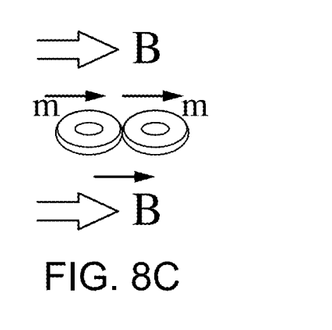
Figure 8D:
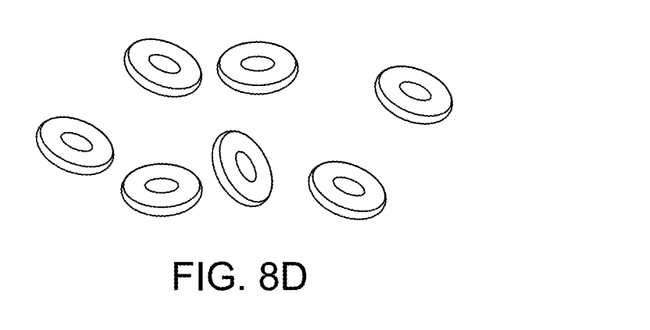

In step 320, the application of the unidirectional magnetic field to the blood is maintained until the rouleaux in the blood are separated. FIGS. 8A, 8B, 8C, and 8D are diagrams of a process to break up and cure rouleaux before and after the performance of steps 310 and 320, respectively. FIG. 8A shows the rouleaux before performance of step 310. FIG. 8B shows that during performance of step 320, the induced dipolar moments of two neighboring red cells in the rouleau exerts a repulsive force to break the rouleau. FIG. 8C shows that during the performance of step 320, after the rouleau is broken, the induced dipolar moments force the red cells to form short chains along the diameter direction. FIG. 8D shows that after the performance of step 320, the magnetic field is turned off, the red cells eventually are freely distributed inside the blood plasma after the short chains in FIG. 8C are broken.

Figure 9A:
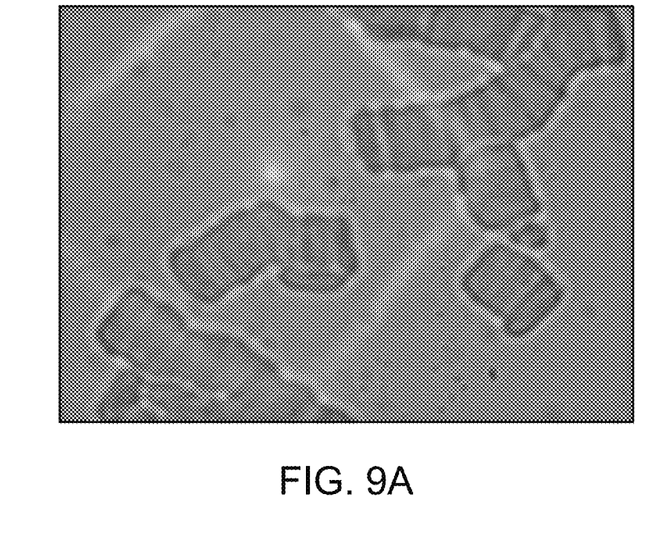
FIGS. 9A and 9B depict red blood cells (a) before and (b) after the treatment of rouleaux depicted in FIG. 7.
Figure 9B:
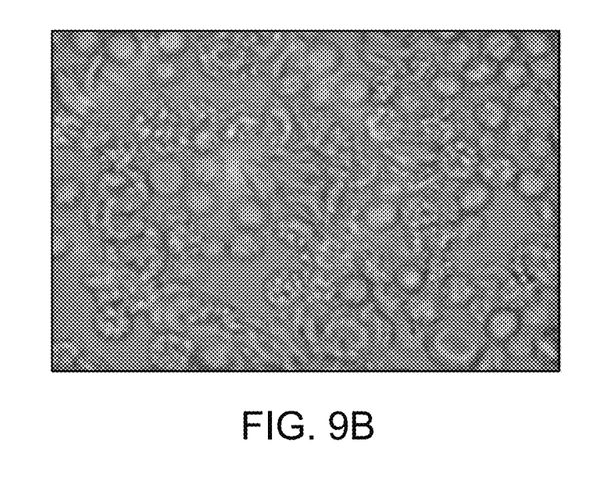

FIGS. 9A and 9B depict red blood cells before and after the performance of step 320, respectively. As shown in FIG. 9A, blood cells have formed rouleaux, or stacks along their major surfaces. As shown in FIG. 9B, the application of the unidirectional magnetic field has caused the rouleaux to be separated. The duration of step 320 necessary to separate the rouleaux is dependent on the severity of the rouleaux (e.g. the number of stacked blood cells or the number of rouleaux), the strength of the unidirectional magnetic field, and the length of time the blood is exposed to the magnetic field.

In an exemplary embodiment, the unidirectional magnetic field has a strength of 1 Tesla or greater, and usually, 1.33 Tesla. The unidirectional magnetic field may be applied to the blood sample for a predetermined period of time, e.g., at least one minutes. Longer periods of time, such as five minutes, ten minutes, fifteen minutes, twenty minutes, thirty minutes, forty minutes, fifty minutes, or up to an hour may also be used in order to separate particularly severe rouleau. In order to treat the rouleaux within all blood inside the patient's whole body with the arrangements in FIGS. 3A-3C, the application of magnetic field may be at least one hour or longer.

In some embodiments, physiological characteristics of the patient may be monitored to determine the efficacy of treatment, and/or whether treatment can be concluded. These characteristics may be observed for either the blood viscosity reduction treatment or the rouleaux treatment. Suitable physiological characteristics include, for example, a patient's heart rate, blood pressure, blood oxygen levels, the presence or absence of systolic ejection murmurs, heartbeat waveforms (e.g. using electrocardiograms) and/or the degree of normal heart function. Additionally, for rouleaux treatment, the blood may be visually examined directly (e.g., under a microscope) to determine the presence or absence of rouleaux. Other suitable physiological characteristics which may be monitored to determine the degree of reduction in blood viscosity or suppression of turbulence will be known to one of ordinary skill in the art from the description herein. Generally, when the blood viscosity is reduced and turbulence is suppressed, the patient's blood pressure will be lowered and heart murmur will be diminished. Thus, when the rouleaux are cured, the patient's blood oxygen function will be improved.

Figure 10A:
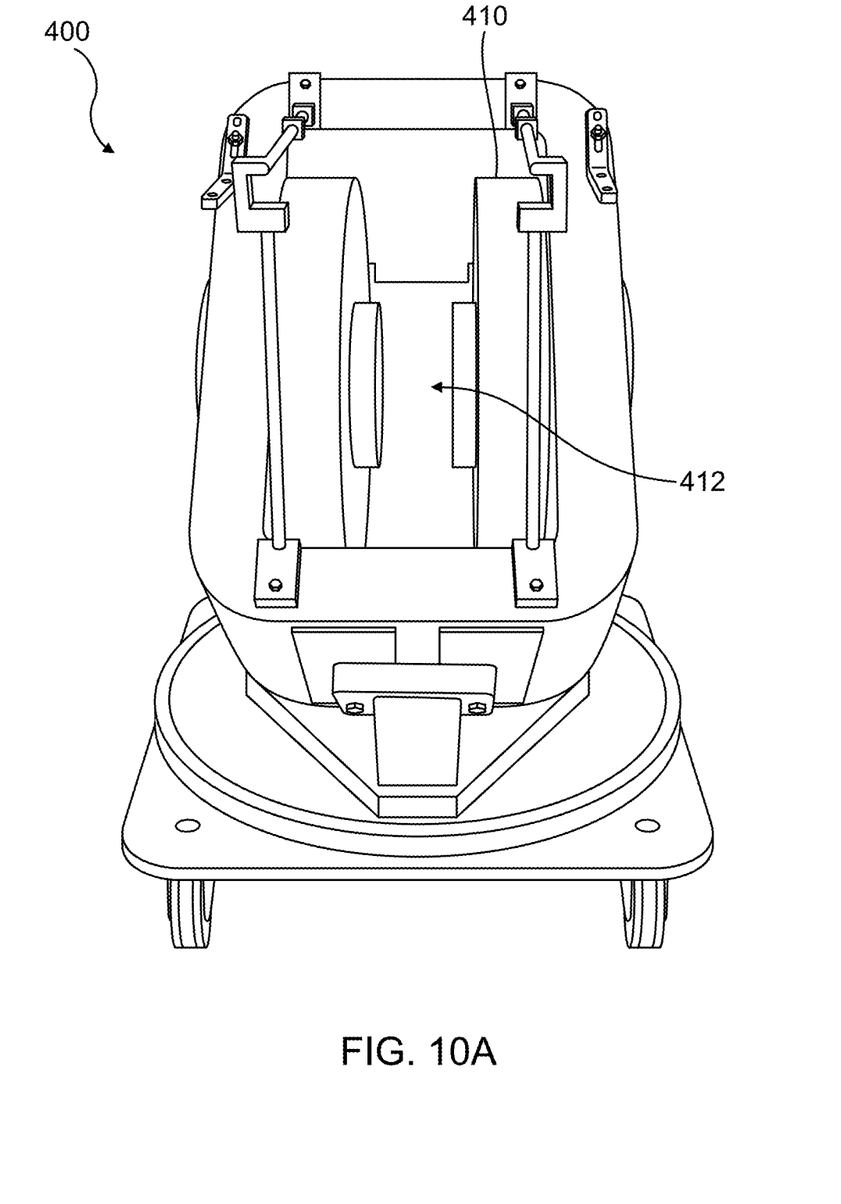
FIGS. 10A and 10B depict another exemplary system for reducing the viscosity of blood flow, suppressing turbulence, and curing rouleaux in accordance with aspects of the present invention.
Figure 10B:
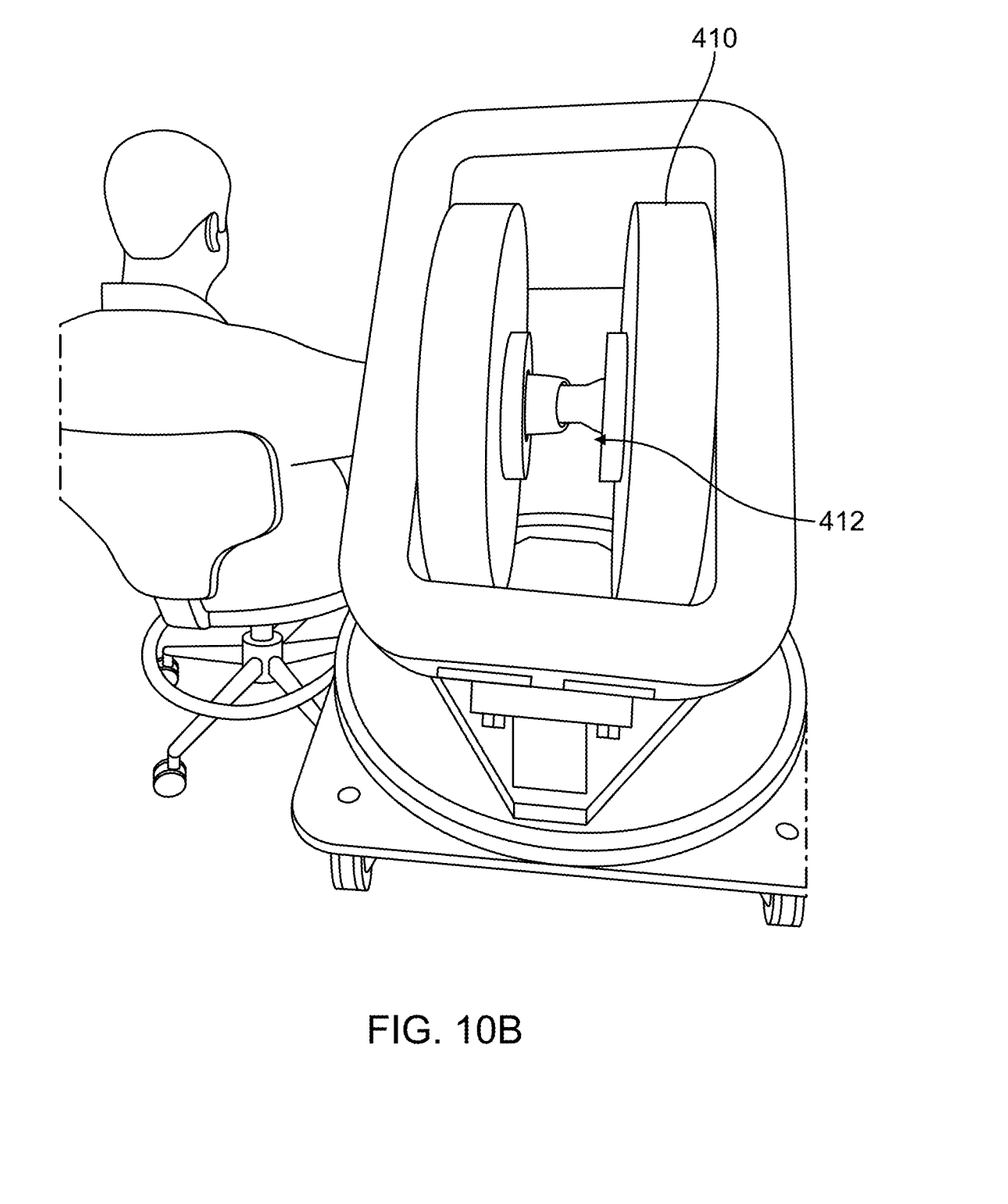

FIGS. 10A and 10B illustrate another system 400 for reducing the blood viscosity and/or suppressing turbulence in blood flow in accordance with aspects of the present invention. System 400 may be usable to treat rouleaux. As a general overview, system 400 includes a magnet 410. Additional details of system 400 are described below.

Magnet 410 is an electromagnet which generates a unidirectional magnetic field. Magnet 410 is an annular (or ring-shaped) magnet defining an axial cavity 412 through the middle thereof. Magnet 410 is adapted to generate the unidirectional field axially through and along the axis of cavity 412 of magnet 410.

As shown in FIG. 10B, cavity 412 of magnet 410 has a size sufficient to receive a portion of the patient's body, i.e., the patient's arm. In this way, the unidirectional magnetic field generated by magnet 410 is applied to a flow of blood within the patient, and more particularly, along the direction of the flow of blood through the patient's arm.

Magnet 410 has a strength sufficient to reduce the blood viscosity in the patient's body by a predetermined amount, and/or to suppress turbulence in the patient's blood flow by a predetermined amount. Magnet 410 may have a strength as set forth above with respect to magnet 110.

EXAMPLES OF THE INVENTION

When blood viscosity along the flow direction is reduced and turbulence is suppressed, laminar blood flow is improved, the workload for the heart is lowered, and blood pressure is reduced. These results are supported by the following example clinical test, the results of which are shown in Table 1. Before a magnetic field was applied, the subject had a blood pressure of 140 mmHg systolic blood pressure and 99 mmHg diastolic blood pressure. The subject then used the system of FIGS. 10A and 10B, in which the subject inserted his right arm into the treatment area. A magnetic field was applied parallel to the blood flow in the arm. After a treatment time of ten minutes, the subject's blood pressure was down to 115/75 mmHg, as shown below.

TABLE 1

| Time | Systolic/Diastolic (mmHg) |
| --- | --- |
| 18:30 | 140/99 (before turning on magnetic field) |
| 18:31 | 138/97 (at turning on of magnetic field) |
| 18:32 | 134/97 |
| 18:33 | 131/96 |
| 18:34 | 136/96 |
| 18:35 | 135/94 |
| 18:36 | 127/85 |
| 18:37 | 131/91 |
| 18:38 | 125/82 |
| 18:39 | 120/80 |
| 18:40 | 115/75 (at turning off of magnetic field) |

Figure 11:
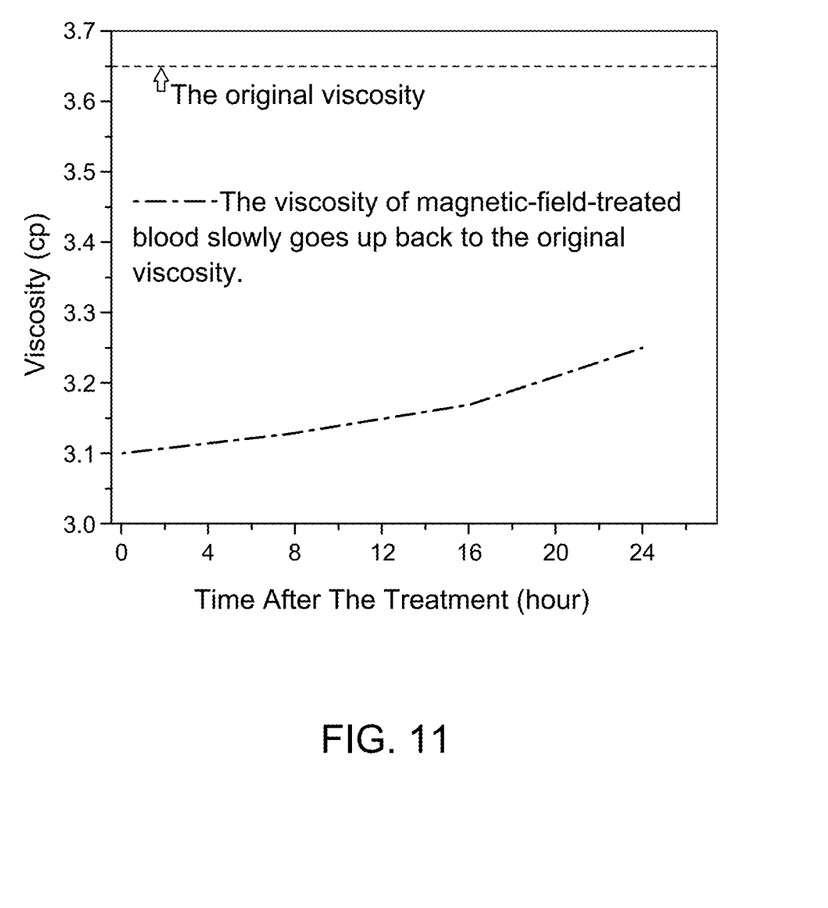
FIG. 11 depicts the duration of reduced viscosity along the flow direction after one magnetic-field treatment.

FIG. 11 depicts the duration of the reduced blood viscosity after one magnetic field treatment. Since the viscosity reduction along the flow direction (a part of the anisotropic viscosity) is the result of aggregated short chains of red cells along the flow direction, the blood viscosity will return to the original isotropic value after the aggregated chains are completely dissembled. Because red cells are soft and elastic, the aggregated short chains make the suspension act as a viscoelastic fluid. Disassembly of such viscoelastic chains by thermal motion is very slow. Therefore, the magnetic field-treated blood can maintain a level of anisotropic viscosity over a period of more than 24 hours after a single magnetic field treatment. As shown in FIG. 11, a blood sample originally had a viscosity of 3.65 centipoise (cp) at 37° C. After treatment by a 1.3 Tesla magnetic field for four seconds, the viscosity was down to 3.10 cp, reduced by 15%. The viscosity remained at or below 3.13 cp up to eight hours after the treatment, at or below 3.17 cp up to sixteen hours after the treatment, and at or below 3.22 cp up to 24 hours after the treatment. These results show that one efficient magnetic field treatment can maintain an effect of reduced viscosity lasting 24 hours or more.

The process is also repeatable. Once the short chains are dissembled, re-application of strong magnetic field to the blood will make the blood viscosity anisotropic again. Therefore, with strong magnetic field treatment once each day, for example, blood viscosity can be kept lower in the flow direction, all turbulences suppressed, and the blood flow laminar.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A method for reducing blood viscosity and/or suppressing turbulence in blood flow comprising:
   applying a unidirectional magnetic field to a flow of blood in a direction parallel or antiparallel to a direction of the flow of blood; and
   maintaining the application of the unidirectional magnetic field to the flow of blood until a blood viscosity along the direction of the flow of blood is reduced by a predetermined amount and/or the turbulence in the blood flow is suppressed by a predetermined amount.

2. The method of claim 1, wherein the unidirectional magnetic field has a strength of 1 Tesla or greater.

3. The method of claim 1, wherein the maintaining comprises maintaining the application of the unidirectional magnetic field for a predetermined period of time.

4. The method of claim 3, wherein the unidirectional magnetic field has a strength of 1.33 Tesla, and the predetermined period of time is at least fifteen minutes.

5. The method of claim 1, wherein the maintaining comprises maintaining the application of the unidirectional magnetic field until chains of blood cells are formed along the direction of the unidirectional magnetic field.

6. The method of claim 1, wherein the blood viscosity along the direction of the flow of blood is reduced to be within a range of 3.0-4.0 cp.

7. The method of claim 1, wherein the unidirectional magnetic field is applied to a limb of a patient.

8. The method of claim 7, wherein the unidirectional magnetic field is applied with an annular magnet encircling the limb of the patient.

9. The method of claim 1, wherein the blood viscosity reduction and/or turbulence suppression will make the blood flow laminar, lower a patient's blood pressure, cure hypertension, diminish heart murmur, and prevent development of astherosclerosis plaque in blood vessels.

10. A system for reducing blood viscosity and/or suppressing turbulence in blood flow comprising:
    an annular magnet sized to encircle a portion of a patient's body, the magnet adapted to generate a unidirectional magnetic field in a region within the annular magnet, the unidirectional magnetic field having a strength sufficient to reduce the blood viscosity in the portion of the patient's body by a predetermined amount and/or suppress turbulence in the blood flow by a predetermined amount.

11. The system of claim 10, wherein the unidirectional magnetic field generated by the annular magnet has a strength of 1 Tesla or greater.

12. The system of claim 11, wherein the annular magnet is sized to encircle a limb of the patient.

13. The system of claim 12, wherein the annular magnet is a magnet selected from a group consisting of an electromagnet, a permanent magnet, and a superconducting magnet.

14. A method for treating rouleaux comprising:
    applying a unidirectional magnetic field to blood containing the rouleaux, wherein the unidirectional magnetic field has a strength of 1 Tesla or greater; and
    maintaining the application of the unidirectional magnetic field to the blood until the rouleaux are separated.

15. The method of claim 14, wherein the maintaining comprises maintaining the application of the unidirectional magnetic field for a predetermined period of time.

16. The method of claim 15, wherein the unidirectional magnetic field has a strength of 1.33 Tesla, and the predetermined period of time is at least one hour.

17. The method of claim 15, wherein the blood is part of a flow of blood within a patient's body.

18. The method of claim 17, wherein the unidirectional magnetic field is applied to a limb of the patient.

19. The method of claim 18, wherein the unidirectional magnetic field is applied with an annular magnet encircling the patient's limb.

20. The method of claim 14, wherein the separation of rouleaux improves a patient's blood oxygen function.

21. A method for treating rouleaux comprising:
    applying a unidirectional magnetic field to a flow of blood within a patient's body containing the rouleaux; and
    maintaining the application of the unidirectional magnetic field to the blood for a predetermined period of time until the rouleaux are separated, wherein the unidirectional magnetic field is applied in a direction parallel or anti parallel to a direction of the flow of blood.

* * * * *